United States Patent
Gross

(10) Patent No.: US 9,420,978 B2
(45) Date of Patent: Aug. 23, 2016

(54) PATIENT SUPPORT APPARATUS AND A MEDICAL IMAGING APPARATUS COMPRISING THE PATIENT SUPPORT APPARATUS

(71) Applicant: Patrick Gross, Buckenhof (DE)

(72) Inventor: Patrick Gross, Buckenhof (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 468 days.

(21) Appl. No.: 13/937,252

(22) Filed: Jul. 9, 2013

(65) Prior Publication Data

US 2014/0013511 A1 Jan. 16, 2014

(30) Foreign Application Priority Data

Jul. 10, 2012 (DE) .......................... 10 2012 212 011

(51) Int. Cl.
*A47B 13/00* (2006.01)
*A61B 6/04* (2006.01)
*A61B 5/055* (2006.01)
*A61B 5/00* (2006.01)

(52) U.S. Cl.
CPC .............. *A61B 6/0407* (2013.01); *A61B 5/0555* (2013.01); *A61B 5/704* (2013.01)

(58) Field of Classification Search
CPC .................. A61B 6/04–6/0492; A61B 5/0555; A61B 5/704
See application file for complete search history.

(56) References Cited

U.S. PATENT DOCUMENTS

| | | | |
|---|---|---|---|
| 6,460,206 B1 | 10/2002 | Blasche et al. | |
| 2006/0142655 A1* | 6/2006 | Petot | A61B 5/0555 600/410 |
| 2007/0171428 A1* | 7/2007 | Dunham | G01B 11/02 356/496 |
| 2010/0034350 A1* | 2/2010 | Vaisburd | A61B 6/4441 378/62 |
| 2011/0145992 A1 | 6/2011 | Gross | |
| 2013/0267883 A1* | 10/2013 | Medrano | A61G 7/015 604/5.01 |
| 2014/0037050 A1* | 2/2014 | Uhlemann | A61B 5/0507 378/20 |
| 2015/0196227 A1* | 7/2015 | Chen | A61B 6/0457 5/601 |

FOREIGN PATENT DOCUMENTS

| | | |
|---|---|---|
| CN | 101023870 A | 8/2007 |
| DE | 19947328 | 5/2001 |
| DE | 102006044620 A1 | 4/2007 |
| DE | 102006040941 A1 | 3/2008 |
| DE | 102007035569 A1 | 1/2009 |
| DE | 102010020923 A1 | 6/2011 |
| DE | 102010027296 A1 | 9/2011 |

* cited by examiner

*Primary Examiner* — David E Sosnowski

(57) ABSTRACT

A patient support apparatus for a medical imaging apparatus includes a base unit and a table, wherein the table is designed so as to be movable relative to the base unit. A position detection apparatus detects a position of the table relative to the base unit, wherein the position detection apparatus has an optical sensor unit which includes a fiber optic element and a punched tape mask. The punched tape mask is movable relative to the optical sensor unit. Optical signals are transmitted via the fiber optic element.

15 Claims, 2 Drawing Sheets

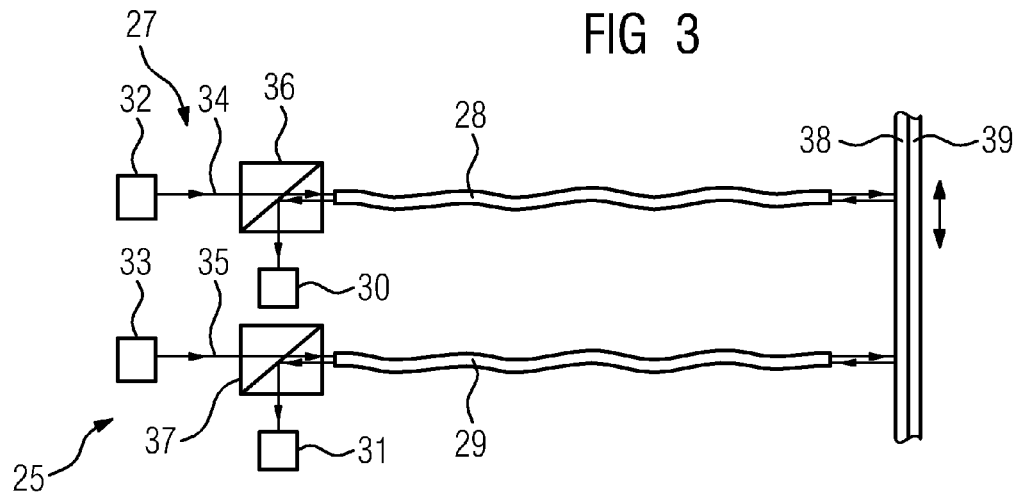
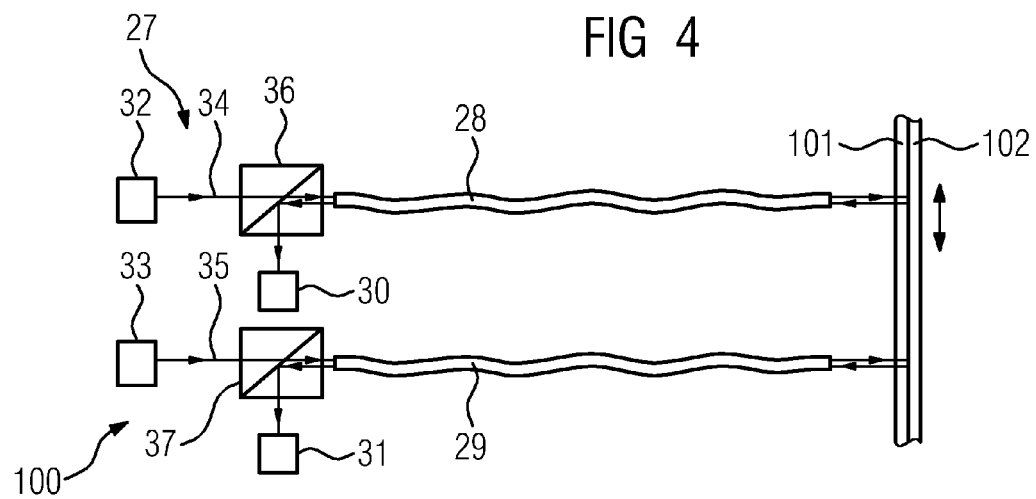
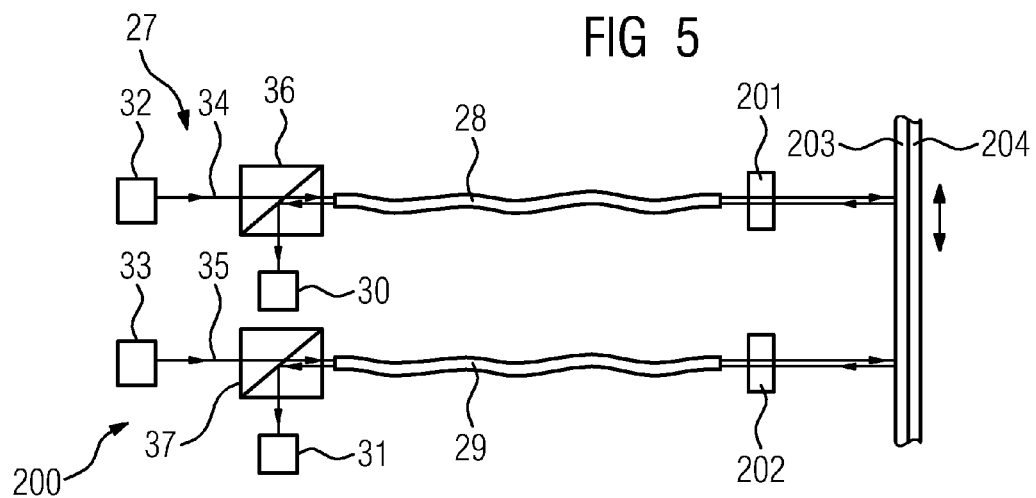

PATIENT SUPPORT APPARATUS AND A MEDICAL IMAGING APPARATUS COMPRISING THE PATIENT SUPPORT APPARATUS

CROSS REFERENCE TO RELATED APPLICATIONS

The present application claims priority to German Patent Application No. 102012212011.4 DE filed Jul. 10, 2012, the entire content of which is hereby incorporated herein by reference.

FIELD OF INVENTION

The present invention relates to a patient support apparatus, for a medical imaging apparatus in particular, having a base unit, a table, wherein the table is designed so as to be movable relative to the base unit, and a position detection apparatus for detection of a position of the table relative to the base unit, wherein the position detection apparatus has an optical sensor unit, which includes a fiber optic element, and a punched tape mask which can be moved relative to the optical sensor unit.

BACKGROUND OF INVENTION

For medical imaging examinations, such as magnetic resonance examinations, exact positioning of the patient within a patient examination area of the medical imaging apparatus is necessary. For this purpose the medical imaging apparatus has in particular a patient support apparatus of the medical imaging apparatus, a position detection apparatus for detection of a position of a table with respect to a base unit of the patient support apparatus. The patient is supported on the table for the medical imaging examination and is moved together with the table into the patient scanning area.

Previous position detection apparatuses include an optical sensor unit and a punched tape mask, which is designed so as to be movable with respect to the optical sensor unit. The optical sensor unit includes at least one first fiber optic element for supplying light signals to the punched tape mask and at least one second fiber optic element for returning light signals which penetrate the punched tape mask. The at least one first fiber optic element is designed separately from the at least one second fiber optic element here. Furthermore, it is customary for a position detection measurement to be made at two different positions, so an absolute position of the table can be determined from the detected signals. As a result of this the position detection apparatus takes up a great deal of space, however, within the patient support apparatus.

SUMMARY OF INVENTION

An object is to provide a patient support apparatus with a position detection apparatus which enables highly accurate position detection in a particularly compact manner. The object is achieved by the features of the independent claims. Advantageous embodiments are described in the dependent claims.

The invention relates to a patient support apparatus, in particular for a medical imaging apparatus, having a base unit, a table, wherein the table is designed so as to be movable relative to the base unit, and a position detection apparatus for detection of a position of the table relative to the base unit, wherein the position detection apparatus has an optical sensor unit, which includes a fiber optic element, and a punched tape mask which can be moved relative to the optical sensor unit.

It is proposed that optical signals are supplied and optical signals are returned by means of the fiber optic element. Installation space inside the patient support apparatus can be particularly advantageously saved hereby since the optical signals are supplied and returned by means of a single fiber optic element. Furthermore, an inexpensive patient support apparatus can also be provided owing to a reduction in components. Furthermore, despite the small installation space, a high level of accuracy can be achieved when detecting the position of the table by means of the punched tape mask. The punched tape mask is preferably designed so it can be move together with the table, or the punched tape mask is arranged on the table. The optical sensor unit on the other hand is preferably arranged on the base unit. In an advantageous embodiment of the invention the punched tape mask has an irregular punched tape pattern, so an item of position information of the table with respect to the base unit can be allocated to each section of the punched tape pattern.

It is also proposed that the punched tape mask has a light-reflecting surface, whereby a position of the punched tape mask with respect to the sensor unit and therewith also a position of the table with respect to the base unit can advantageously be determined with the aid of a light pattern reflected by the punched tape mask and detected by the sensor unit.

In an alternative embodiment of the invention it is proposed that the position detection apparatus has an optical background element which is arranged after the punched tape mask along a radiation path from the fiber optic element to the punched tape mask and which has a light-reflecting surface. The punched tape mask preferably includes a non-reflecting surface here, so a position of the punched tape mask with respect to the sensor unit and therewith a position of the table with respect to the base unit can advantageously be detected with the aid of a light pattern reflected and detected by the background element.

It is also proposed that the position detection apparatus has an optical background element which is arranged after the punched tape mask along a radiation path from the fiber optic element to the punched tape mask, wherein the background element or the punched tape mask has a light-absorbing surface. In an embodiment of the background element having a reflective surface and the punched tape mask having a light-absorbing surface a random reflection through a surface of the punched tape mask can advantageously be prevented and therefore the light signals reflected by the background element can be unambiguously allocated to the punched tape pattern. Similarly, with an embodiment of the punched tape mask having a reflective surface and of the optical background element with a light-absorbing surface a random reflection through the surface of the background element can advantageously be prevented and therefore the light signals reflected by the punched tape mask can be unambiguously allocated to the punched tape pattern.

If the light-reflecting surface and/or the light-absorbing surface of the punched tape mask and/or the optical background element are configured for frequency-dependent light reflection and/or for a frequency-dependent light absorption, undesirable background signals and/or undesirable background noise can advantageously be suppressed, so the reflected and detected light signals can be particularly easily allocated to a punched tape pattern of the punched tape card.

In a further embodiment of the invention it is proposed that the optical sensor unit has at least two fiber optic elements by way of which optical signals are supplied and returned respectively during operation of the position detection apparatus, wherein the at least two fiber optic elements are arranged at different positions. The two fiber optic elements preferably have a fixed, in particular constant, spacing from each other. A position, in particular an absolute position, of the punched tape mask and therewith of the table with respect to the base unit can be detected particularly easily and effectively in this way since a speed of the punched tape mask and/or of the table with respect to the optical sensor unit and/or with respect to the base unit can be taken into account in this connection.

A particularly compact and space-saving position detection apparatus can be achieved if the optical sensor unit has at least one beam splitter element. The beam splitter element preferably has a semi-transparent mirror, so by means of the beam splitter element an advantageous division can be achieved between the incoming beam and the returning beam. The at least one beam splitter element is preferably arranged along a radiation path between the fiber optic element and a detector unit and/or a light source unit.

Advantageous signal detection and a particularly compact position detection apparatus can be achieved if the optical sensor unit has at least one detector element. Furthermore, effective, in particular optical, coordination can be achieved between a light source and the detector.

Particularly advantageous focusing of the incoming light beam can be achieved if the position detection apparatus has at least one laser light source. For this purpose the position detection apparatus particularly advantageously also has a lens unit which is arranged between the fiber optic element and the punched tape mask. It may be advantageous for a spacing between the punched tape mask and the fiber optic element to be increased and an installation space for the position detection apparatus to advantageously be minimized thereby and/or to be adapted to further components and/or units of the patient support apparatus. The lens unit is preferably arranged directly after the fiber optic element along a radiation path from the fiber optic element to the punched tape mask, so advantageous focusing of the beam directed onto the punched tape mask can be achieved onto the punched tape mask, moreover. Furthermore, advantageous focusing of the beam reflected at the punched tape mask and/or the optical background element, and/or reflected beam portion onto the fiber optic element can be achieved.

The invention also relates to a medical imaging apparatus comprising a detector unit, a patient examination area at least partially surrounded by the detector unit and a patient support apparatus as claimed in any one of claims 1 to 10. A particularly compact position detection apparatus for detecting a position of the patient support apparatus, in particular a table of the patient support apparatus, within the patient examination area can be achieved, so an exact position of the patient is always available for the pending medical imaging examination. The base unit preferably has a fixed position with respect to the medical imaging apparatus, in particular the patient examination area of the medical imaging apparatus, so the position of the table with respect to the patient examination area can be particularly easily determined with the aid of the position of the table with respect to the base unit.

It is also proposed that the medical imaging apparatus has a data processing unit for determining a position of the table with respect to the detector unit with the aid of the data from the position detection apparatus, whereby direct and fast position determination of the table can be achieved with respect to the base unit and/or the patient examination area.

BRIEF DESCRIPTION OF THE DRAWINGS

Further advantages, features and details of the invention emerge from the exemplary embodiments described below and with reference to the drawings, in which:

FIG. 3 shows a first exemplary embodiment of a position detection apparatus in a schematic diagram, FIG. 4 shows a second exemplary embodiment of the position detection apparatus in a schematic diagram and FIG. 5 shows a third exemplary embodiment of the position detection apparatus in a schematic diagram.

DETAILED DESCRIPTION OF INVENTION

Figure 1:
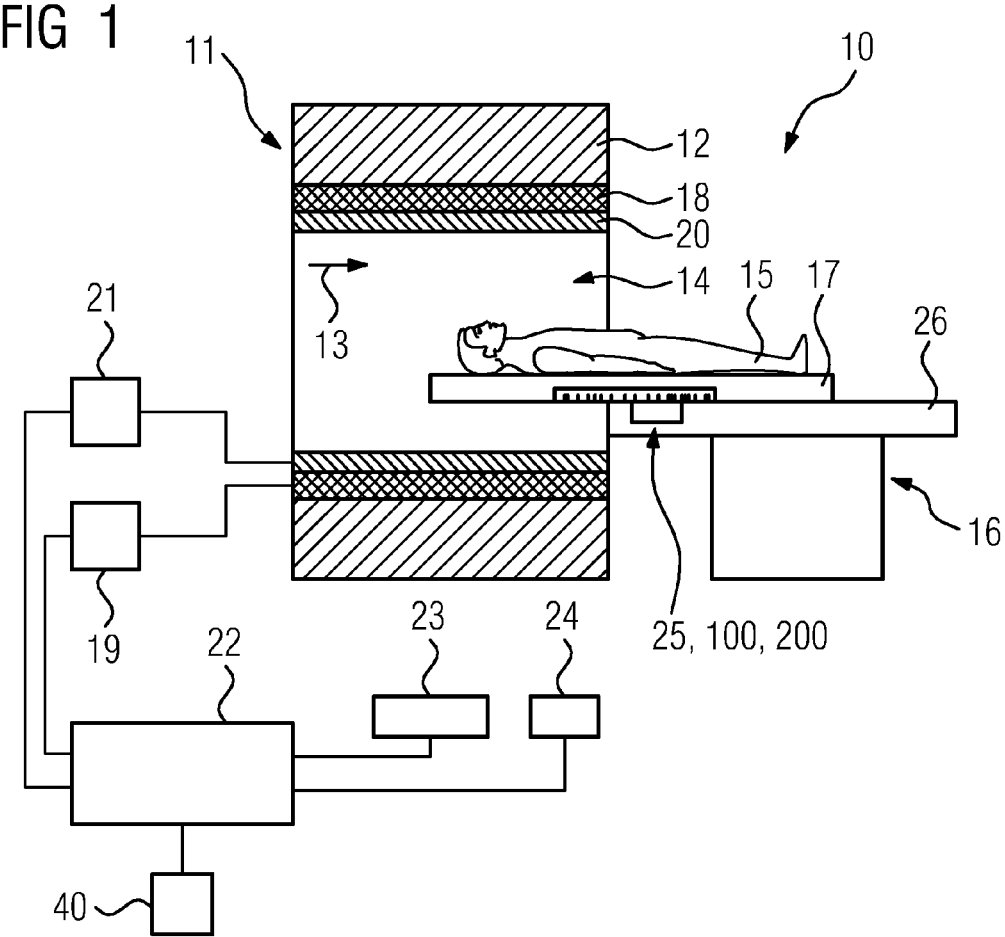
FIG. 1 shows a medical imaging apparatus in a schematic diagram.

FIG. 1 schematically shows an inventive medical imaging apparatus which is formed by a magnetic resonance apparatus 10. The medical imaging apparatus can, moreover, also be formed by a computed tomography apparatus, a PET (Positron Emission Tomography) apparatus, an AX arm, etc.

The magnetic resonance apparatus 10 includes a detector unit formed by a magnetic unit 11, having a main magnet 12 for generating a strong and in particular constant main magnetic field 13. The magnetic resonance apparatus 10 also has a cylindrical patient examination area 14 for scanning a patient 15, wherein the patient examination area 14 is enclosed in a circumferential direction by the magnetic unit 11. The patient 15 can be pushed by means of a patient support apparatus 16 of the magnetic resonance apparatus 10 into the patient examination area 14. The patient support apparatus 16 has a table 17 for this purpose which is movably arranged inside the magnetic resonance apparatus 10, in particular the patient receiving area 15.

The magnetic unit 11 also has a gradient coil unit 18 for generating magnetic field gradients, which is used for spatial encoding during imaging. The gradient coil unit 18 is controlled by means of a gradient control unit 19. The magnetic unit 11 also has a high frequency antenna unit 20 and a high frequency antenna control unit 21 for exciting a polarization which is established in the main magnetic field 13 generated by the main magnet 12. The high frequency antenna unit 20 is controlled by the high frequency antenna control unit 21 and irradiates high frequency magnetic resonance sequences into an examination space which is substantially formed by the patient examination area 14.

For controlling the main magnet 12, the gradient control unit 19 and for controlling the high frequency antenna control unit 21 the magnetic resonance apparatus 10 has a control unit 22 formed by an arithmetic unit. The control unit 22 centrally controls the magnetic resonance apparatus 10, such as by way of example the execution of a predetermined imaging gradient echo sequence. Control information, such as imaging parameters, and reconstructed magnetic resonance images can be displayed on a display unit 23, by way of example on at least one monitor, of the magnetic resonance apparatus 10 for an operator. Furthermore, the magnetic resonance apparatus 10 has an input unit 24 by means of which an operator can input information and/or parameters during a measuring process.

The illustrated magnetic resonance apparatus 10 can of course include further components which magnetic resonance apparatuses 10 conventionally have. A general mode of operation of a magnetic resonance apparatus 10 is known to the person skilled in the art, moreover, so a detailed description of the general components is being omitted.

Figure 2:
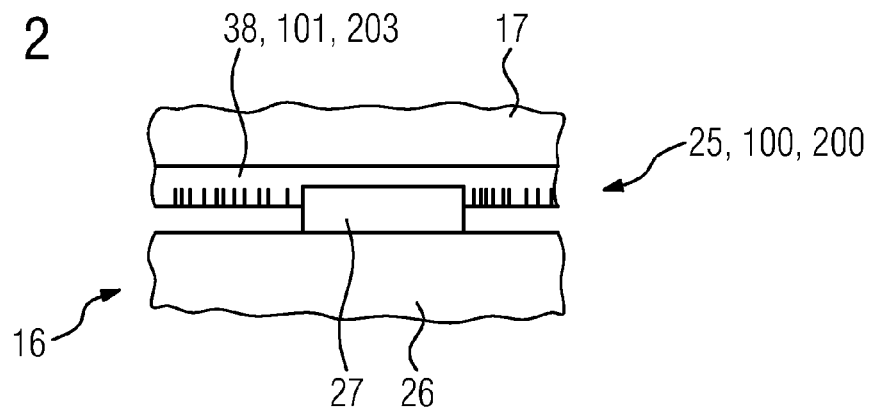
FIG. 2 shows a section of a patient support apparatus with the position detection apparatus.

For medical imaging examinations, in particular magnetic resonance examinations, it is necessary for the patient 15, in particular an area of the patient 15 to be examined, to be arranged as exactly as possible in a focal point of a detector unit, in particular the magnetic unit 11, of the medical imaging apparatus. For this purpose the patient support apparatus 16 has a position detection apparatus 25, 100, 200, by means of which a position of the table 17 with respect to a base unit 26 of the patient support apparatus 16 and/or with respect to the patient examination area 14 can be determined and/or detected, as is shown in more detail in FIG. 2.

A first exemplary embodiment of the position detection apparatus 25 is shown in more detail in FIG. 3. The position detection apparatus 25 has an optical sensor unit 27 which has two fiber optic elements 28, 29, two detector elements 30, 31 and two light sources 32, 33. The light sources 32, 33 each have a laser light source. As an alternative to this an embodiment of the light sources 32, 33 which is different from a laser light source is always conceivable. The two fiber optic elements 28, 29 are arranged at a distance from each other on the base unit 26. The two detector elements 30, 31 and the two light sources 32, 33 are, moreover, likewise arranged on the base unit 26. A light beam 34, 35 is in each case generated by means of the laser light sources and this is introduced into the fiber optic elements 28, 29 in each case. Returning and/or reflected beams are also each guided by means of the two fiber optic elements 28, 29 to the two detector elements 30, 31.

The two detector elements 30, 31 and the laser light sources are arranged on the same side, in particular on the same light entry side of the two fiber optic elements 28, 29, so during operation of the position detection apparatus 25 advancing laser light beams 34, 35 and returning laser light beams 34, 35 are simultaneously transported and/or conveyed in the two fiber optic elements 28, 29. One beam splitter element 36, 37 respectively is arranged, moreover, between the laser light sources or the detector elements 30, 31 and the fiber optic elements 28, 29. The laser light beam emitted by the laser light sources is introduced into the fiber optic elements 28, 29 by means of the beam splitter elements 36, 37, wherein for this purpose the beam splitter elements 28, 29 are constructed and/or designed in such a way that optimally loss-free introduction of the laser light beams into the fiber optic elements 28, 29 is enabled.

Furthermore, the beams returning through the fiber optic elements 28, 29 are deflected at the beam splitter elements 36, 37 in such a way that they strike the detector units 30, 31 and are detected there. For this purpose the beam splitter elements 36, 37 include by way of example one semi-transparent mirror element respectively.

The position detection apparatus 25 also has a punched tape mask 38 which is arranged on the table 17 and therefore the punched tape mask 38 is movably arranged with respect to the fiber optic elements 28, 29 and detector elements 30, 31. In the present exemplary embodiment the punched tape mask 38 has an irregular punched tape pattern. The position detection apparatus 25 also has an optical background element 39 which is arranged behind the punched tape mask 38 along a radiation path from the fiber optic elements 28, 29 to the punched tape mask 38.

In the present exemplary embodiment the punched tape mask 38 has a light-reflecting surface and the optical background element 39 a light-absorbing surface.

The laser light beams generated by the laser light sources are introduced by means of the beam splitter elements 36, 37 into one of the fiber optic elements 28, 29 respectively and by means of the fiber optic elements 28, 29 are guided to the punched tape mask 38, wherein the punched tape mask 38 is spaced apart from light outlet openings of the fiber optic elements 28, 29. The laser light issuing from the fiber optic elements 28, 29 is reflected at the punched tape mask 38, in particular at the light-reflecting surface of the punched tape mask 38. The light-absorbing surface of the optical background element 39 absorbs the laser light passing through the punched tape mask 38, so only the laser light reflected by the punched tape pattern of the punched tape mask 38 is radiated back to the fiber optic elements 28, 29 and by means of the fiber optic elements 28, 29 and beam splitter elements 36, 37 is guided to the two detector units 30, 31.

The magnetic resonance apparatus 10 also has a data evaluation unit 40 which determines a position of the table 17 within the patient examination area 14 from the data and/or signals detected by the detector elements 30, 31. The detected data and/or signals are transferred by means of a data transfer unit (not shown in detail) from the two detector elements 30, 31 to the data evaluation unit 40. The light pattern detected by means of the detector elements 30, 31 reflects the punched tape pattern of the punched tape mask 38, wherein an item of position information is allocated to each section of the punched tape pattern. By means of the two detector elements 30, 31 and the two fiber optic elements 28, 29, which carry out a position measurement at different positions of the punched tape mask 38, a speed of the punched tape mask 38 or table 17 with respect to the base unit 26 is also taken into account for calculation of the position, so an absolute position of the table 17 can be determined inside the data evaluation unit 40 in this way.

Furthermore it can be provided that the light-reflecting surface of the punched tape mask 38 and/or the light-absorbing surface of the optical background element 39 is designed in such a way that only frequency-dependent light reflection and/or a frequency-dependent light absorption is possible. Undesirable background signals in the detected signals are also suppressed and/or reduced in this way.

FIG. 4 schematically shows a position detection apparatus 100 designed as an alternative to FIG. 3. The following description is substantially limited to the differences to the exemplary embodiment in FIG. 3, wherein reference is made with respect to the same components, features and functions to the description of the exemplary embodiment in FIG. 3. Substantially the same components, features and functions are basically numbered with the same reference numerals.

In this exemplary embodiment the punched tape mask 101 of the position detection apparatus 100 has a light-absorbing surface. Furthermore, the optical background element 102 of the position detection apparatus 100 has a light-absorbing surface, so a laser light image inverse to the punched tape mask 101 is detected at the detector elements 30, 31. The remaining embodiment and mode of operation of the position detection apparatus 100 is constructed analogously to the embodiments in FIG. 3.

It may also be provided that the light-absorbing surface of the punched tape mask 101 and/or the light-reflecting surface of the optical background element 102 is designed in such a way that only frequency-dependent light reflection and/or a frequency-dependent light absorption is possible.

FIG. 5 schematically shows a position detection apparatus 200 designed as an alternative to FIGS. 3 and 4. The following description is substantially limited to the differences to the exemplary embodiment in FIGS. 3 and 4, wherein reference is made with respect to the same components, features and functions to the description of the exemplary embodiment in FIGS. 3 and 4. Substantially the same components, features and functions are basically numbered with the same reference numerals.

The position detection apparatus 200 here has two lens units 201, 202 which are arranged between the fiber optic elements 28, 29 and the punched tape mask 203. The beam issuing from fiber optic elements 28, 29 is focused by means of the lens units 201, 202 onto the punched tape mask 203 and a beam reflected by the punched tape mask 203 and/or the optical background element 204 is also focused by means of the lens units 201, 202 onto the entry openings of the fiber optic elements 28, 29. The remaining embodiment and mode of operation of the position detection apparatus 100 is constructed analogously to the embodiments in FIG. 3 or 4.

The invention claimed is:

1. A patient support apparatus for a medical imaging apparatus, comprising:
    a base unit,
    a table, wherein the table is designed so as to be movable relative to the base unit, and
    a position detection apparatus for detecting of a position of the table relative to the base unit,
    wherein the position detection apparatus comprises an optical sensor unit which includes
        a fiber optic element and
        a punched tape mask which is moveable relative to the optical sensor unit,
    wherein optical signals are supplied and returned via the fiber optic element.

2. The patient support apparatus as claimed in claim 1, wherein the punched tape mask has a light-reflecting surface.

3. The patient support apparatus as claimed in claim 1, wherein the position detection apparatus comprises an optical background element which is arranged after the punched tape mask along a radiation path from the fiber optic element to the punched tape mask and which has a light-reflecting surface.

4. The patient support apparatus as claimed in claim 1,
    wherein the position detection apparatus comprises an optical background element which is arranged after the punched tape mask along a radiation path from the fiber optic element to the punched tape mask, and
    wherein the background element or the punched tape mask has a light-absorbing surface.

5. The patient support apparatus as claimed in claim 2, wherein the light-reflecting surface is configured for frequency-dependent light reflection and/or frequency-dependent light absorption.

6. The patient support apparatus as claimed in claim 4, wherein the light-absorbing surface of the punched tape mask is configured for frequency-dependent light reflection and/or frequency-dependent light absorption.

7. The patient support apparatus as claimed in claim 3, wherein the optical background element is configured for frequency-dependent light reflection and/or frequency-dependent light absorption.

8. The patient support apparatus as claimed in claim 4, wherein the optical background element is configured for frequency-dependent light reflection and/or frequency-dependent light absorption.

9. The patient support apparatus as claimed in claim 1,
    wherein the optical sensor unit comprises at least two fiber optic elements for supplying and returning optical signals during operation of the position detection apparatus,
    wherein the at least two fiber optic elements are arranged at different positions.

10. The patient support apparatus as claimed in claim 1, wherein the optical sensor unit comprises at least one beam splitter element.

11. The patient support apparatus as claimed in claim 1, wherein the optical sensor unit comprises at least one detector element.

12. The patient support apparatus as claimed in claim 1, wherein the position detection apparatus comprises at least one laser light source.

13. The patient support apparatus as claimed in claim 1, wherein the position detection apparatus comprises a lens unit which is arranged between the fiber optic element and the punched tape mask.

14. A medical imaging apparatus, comprising:
    a detector unit,
    a patient examination area at least partially surrounded by the detector unit, and
    a patient support apparatus, comprising:
        a base unit,
        a table, wherein the table is designed so as to be movable relative to the base unit, and
        a position detection apparatus for detecting of a position of the table relative to the base unit,
        wherein the position detection apparatus comprises an optical sensor unit which includes
            a fiber optic element and
            a punched tape mask which is moveable relative to the optical sensor unit,
        wherein optical signals are supplied and returned via the fiber optic element.

15. The medical imaging apparatus as claimed in claim 14, further comprising:
    a data processing unit for determining a position of the table with respect to the detector unit using data from the position detection apparatus.

* * * * *